US00PP15236P2

(12) United States Plant Patent
Heims

(10) Patent No.: US PP15,236 P2
(45) Date of Patent: Oct. 19, 2004

(54) ***LOBELIA* PLANT NAMED 'LILAC CANDLES'**

(50) Latin Name: *Lobelia siphilitica*
Varietal Denomination: Lilac Candles

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 63 days.

(21) Appl. No.: 10/611,580

(22) Filed: Jun. 30, 2003

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—June Hwu
(74) *Attorney, Agent, or Firm*—Klarquist Sparkman, LLP

(57) ABSTRACT

A new and distinct cultivar of *Lobelia* plant characterized by a dwarf habit, and strong, short flowering stems of numerous lilac-colored flowers.

1 Drawing Sheet

Botanical classification: *Lobelia siphilitica.*
Variety denomination: 'Lilac Candles'.

BACKGROUND OF THE INVENTION

The present invention relates to a new and distinct *Lobelia siphilitica* and given the cultivar name 'Lilac Candles'. *Lobelia* is in the family *Lobeliaceae*. This new cultivar originated from several generations of open pollinations between select dwarf *Lobelia siphilitica.*

This plant is unique due to its combination of dwarf habit and congested heads of lilac-colored flowers. It is characterized by the following:

1. Dwarf habit.
2. Numerous lilac-colored flowers.
3. Strong, short flowering stems that don't fall over.

The new variety has been reproduced only by asexual propagation (cuttings and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a two-year-old *Lobelia* 'Lilac Candles' growing in the trial fields in August in Canby, Oreg.

DETAILED PLANT DESCRIPTION

The following is a detailed description of the new *Lobelia* based on observations of a two-year-old specimen grown in the field in Canby, Oreg. The color descriptions are all based on The Royal Horticultural Society Colour Chart.

Botanical name: *Lobelia siphilitica.*
Cultivar name: 'Lilac Candles'.
Parentage: *Lobelia siphilitica* compact forms in Open Pollination.

Plant:
- *Type.*—Herbaceous perennial.
- *Hardiness.*—USDA Zones 4 to 9.
- *Size.*—40 cm wide and 35 cm tall.
- *Form.*—Basal clump.

Leaf:
- *Type.*—Simple.
- *Shape.*—Obovate.
- *Arrangement.*—Rosette to alternate up flowering stem.
- *Blade length.*—8.5 cm.
- *Blade width.*—5.8 cm.
- *Margins.*—Irregularly serrate.
- *Apex.*—Obtuse to acute.
- *Base.*—Attenuate.
- *Texture.*—Smooth.
- *Surface.*—Matte.
- *Vestiture.*—Sparsely pubescent.
- *Venation.*—Pinnate.
- *Petiole length.*—4 to 7 cm.
- *Color.*—Topside — Green 137A. Bottom — Closest to Green 138B.

Inflorescence:
- *Type.*—Terminal raceme.
- *Peduncle.*— Height: 35 cm. Diameter: 5 to 7 mm. Vestiture: Glabrous to sparsely pubescent. Color: Yellow Green 144A.
- *Pedicel.*— Length: 7 mm. Texture: Sparsely pubescent. Color: Yellow Green 144B.
- *Flower number.*—80 to 100 per raceme with secondary flowers later in the leaf axils.

Flower bud:
- *Size.*—19 mm deep and 6 mm wide.
- *Shape.*—Oblong, tube-like on bottom ⅔ then constricted and top ovoid with an acute tip.
- *Color.*—Lavender, Violet Blue 91A to B with yellow green after the constriction, Yellow Green 150C.

Flower:
- *Type.*—Zygomorphic.
- *Shape.*—Bilabiate.
- *Size.*—2.5 cm deep and 1.8 cm wide.
- *Corolla.*—Slit ⅞ down on the upper side between the two upper lobes, upper lobes recurve and are 11 mm long and 4 mm wide. Lower three lobes close together and 10 mm long and 3 mm wide. Tube is 14 mm long and 8 mm wide.

*Texture.*—Satiny.
*Color.*—Lavender, Violet Blue 92A to 91C.
*Calyx.*—5 deeply cut acuminate lobes, linear lanceolate, parted to corolla base.
*Calyx lobe size.*—15 mm deep and 6 mm wide at base.
*Calyx color.*—Green 137A.
*Pistil.*—2 cm. long, Yellow Green 145B.
*Stamen number.*—5 in a column around the stigma.
*Filament length.*—1.7 cm.
*Anther size before dehiscing.*—0.5 cm.
*Pollen color.*—Yellow 11A.
*Bloom period.*—July and August in Canby, Oreg.
*Fragrance.*—None.

Fruit:
*Number.*—50 to 100 per raceme.
*Shape.*—Ovoid.
*Size.*—9 mm wide and 8 mm deep.
*Type.*—Dehiscent capsule.
*Color.*—Tan, Grey Brown 199D.

Seed:
*Size.*—0.5 mm.
*Color.*—Black 202A.
*Shape.*—Ovoid.
*Fertility.*—Fertile.

Pest resistance: No observed pest resistance.

Disease: *Lobelia* are susceptible to rust, smut, and leaf spots. None of these have been observed on plants grown under commercial conditions in Canby, Oreg.

COMPARISONS TO SIMILAR *LOBELIA*

Compared to the species, *Lobelia siphilitica, Lobelia siphilitica* 'Lilac Candles' is much more compact and with many more flowers congested together on the flowering stems. The flowers are lilac-colored rather than blue, there are also more flowering stems than usual.

Compared to *Lobelia siphilitica* compact forms used for the open pollination, this new variety is lilac-colored rather than blue, and has superior flower number.

I claim:

1. A new and distinct cultivar of *Lobelia siphilitica* plant substantially as shown and described.

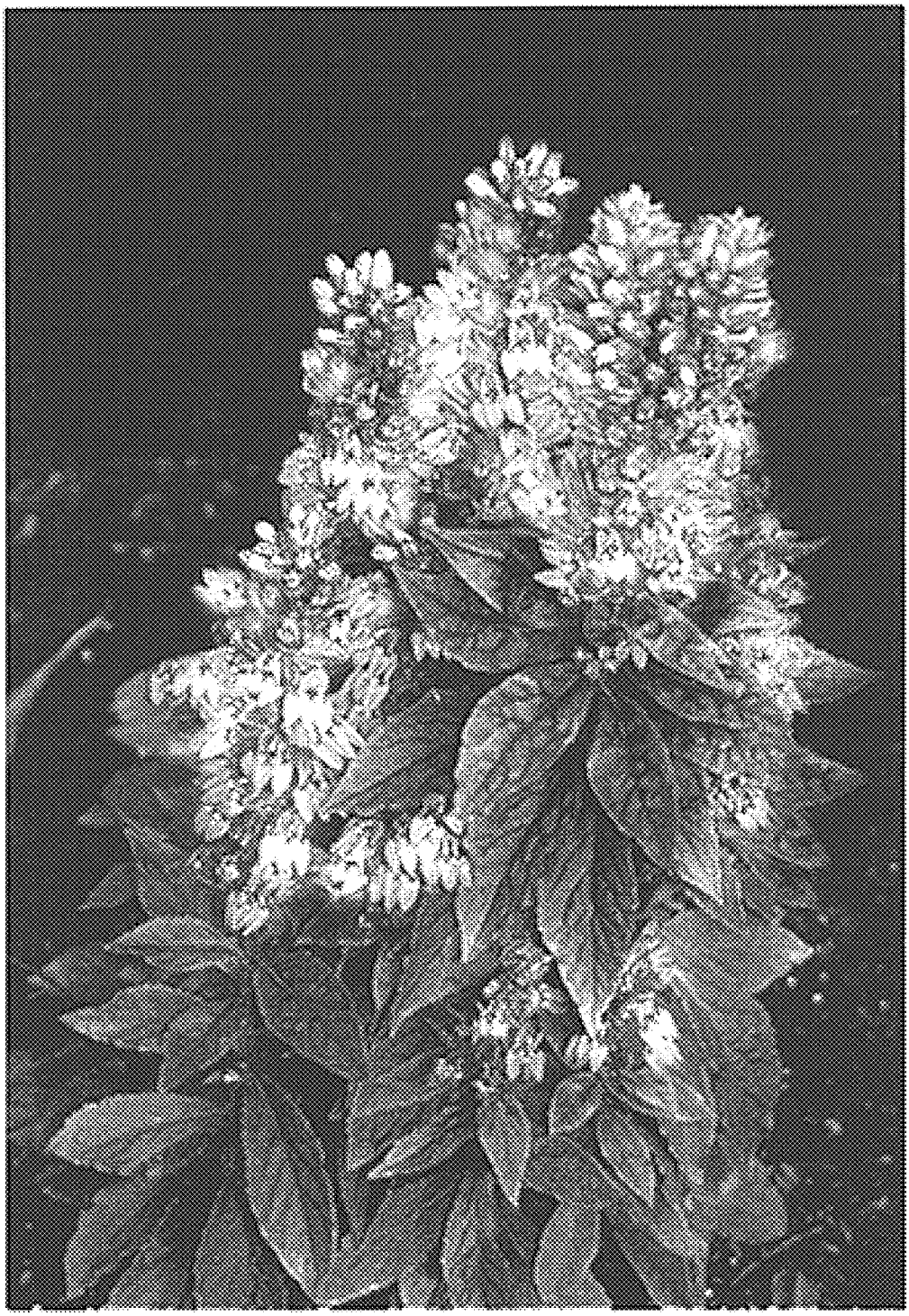

* * * * *